United States Patent [19]

Uemura et al.

[11] Patent Number: 4,835,176

[45] Date of Patent: May 30, 1989

[54] GLYCOOKADAIC ACID, PREPARATION THEREOF AND USE THEREOF

[75] Inventors: Daisuke Uemura, Shizuoka; Toshihiro Yamamoto, Nishinomiya; Takeshi Watanabe, Shimizu; Masanori Okanishi, Kawasaki; Yoshimasa Hirata, Nagoya, all of Japan

[73] Assignee: Banyu Pharmaceutical Co., Ltd., Japan

[21] Appl. No.: 24,752

[22] Filed: Mar. 11, 1987

[51] Int. Cl.$^4$ ............... A61K 31/35; C07D 311/00
[52] U.S. Cl. ................... 514/456; 549/344
[58] Field of Search ............ 514/456; 549/346

[56] References Cited

PUBLICATIONS

Tachibana et al., JACS, 103, 2469–2471 (1981).
Oliff et al., Cell, vol. 50, 555–563 (1987).

*Primary Examiner*—Nicky Chan
*Attorney, Agent, or Firm*—Wegner & Bretschneider

[57] ABSTRACT

The present invention provides glycookadaic acid or salts thereof, processes for the preparation of such compounds, methods for treating and preventing cachexia and a side effect caused by TNF, and pharmaceutical compositions comprising such compounds as active components for treating and preventing cachexia and a side effect caused by TNF.

3 Claims, 3 Drawing Sheets

GLYCOOKADAIC ACID, PREPARATION THEREOF AND USE THEREOF

BACKGROUND OF THE INVENTION

1. Field of the Invention

This invention relates to a novel compound, glycookadaic acid and its salt, its preparation and its use, in particular, treating or preventing cachexia and a side effect caused by TNF.

2. Description of Related Art

Cachexia is a state of serious symptoms caused by cancer and infective disease such as fervescence, chills, trepidation, weight reduction, inappetence, hypotension, decrease in plasma protein, general lassitude, decrease in fat and the like.

Treatment of cachexia relies only on transfusion therapy to recover the whole body state, at present, and there are neither good methods of treatment nor any specific medicines therefor. Thus there have been demanded medicines for treating and preventing cachexia.

Old et al. found that when endotoxin is injected in mice immunized with BCG (Bacille de Calmette et Guerin), a substance causing hemorrhagic necrosis in tumor nodules induced by subcutaneous implantation of tumor cells increases in serum.

This substance was isolated and named "tumor necrosis factor" (TNF). TNF is a physiologically active substance produced by macrophages, and it was thought that TNF shows cytotoxic effect on malignancy cells, but does not adversely affect normal cells (Carswell, E.A. et al., Proc. Natl. Acad. Sci. USA, Vol. 72, pp. 3666–3670 (1975)). The TNF has been recently called TNFα (Wong, G.H.W. et al., Nature, 323, 819–822 (1986)).

On the other hand, it is recently reported that cachectin which has been studied as a factor elevating plasma lipid in the case of infective diseases is substantially the same substance as TNF (Beutler, B. et al., J. Exp. Med., 161, 984–995 (1985)).

Further, it is suggested that cachectin is possibly a cause of a part of syndromes of endotoxin shock upon infection of gram-negative bacteria (Beutler, B, et al., Nature, 316, 552–554 (1985)).

In addition, in a Phase I clinical study of recombinant human-tumor necrosis factor (rHu-TNF) there were observed adverse reactions such as mostly fever, chills, trepidation, and, at a lesser rate, hypotension, elevation of GOT/GPT, general fatigue, elevation of ALP, pain in the extremities, decrease in platelets, and the like, and further, in some cases elevation of neutral lipid in plasma was also observed (Taguchi, T., Jpn. J. Cancer Chemother., 13, 3491–3497 (1986)).

In view of the foregoing the cachexia-like side effects of IF are an important problem in the course of developing TNF as an anticancer drug.

The present inventors have conducted wide screening of compounds for preventing or treating cachexia and for decreasing or preventing side effects of TNF and found that glycookadaic acid of the formula [I](infra) isolated from *Halichondria okadai* Kadota is effective for preventing or treating cachexia and further for decreasing or preventing side effects of TNF.

SUMMARY OF THE INVENTION

The present invention provides glycookadaic acid of the formula,

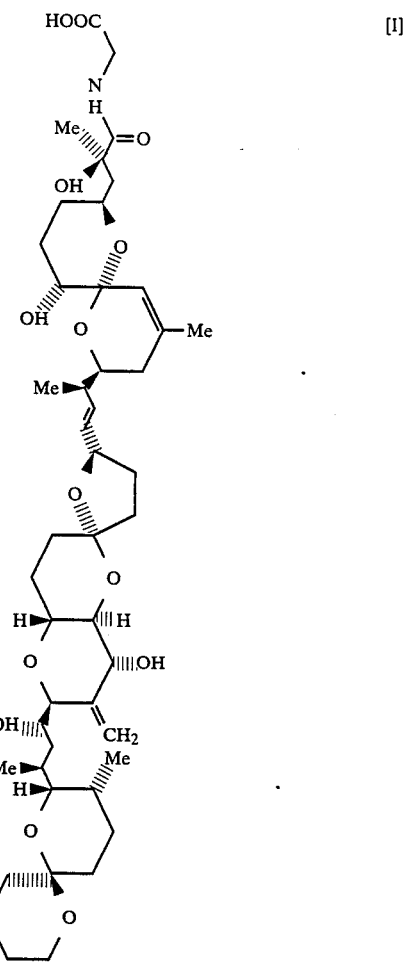

or a pharmaceutically acceptable salt thereof.

According to another aspect of the present invention, there is provided a process for preparing glycookadaic acid by extracting said compound from *Halicondria okadai* Kadota.

According to a further aspect of the present invention, there is provided a process for preparing glycookadaic acid and salts thereof by reacting a compound of the formula,

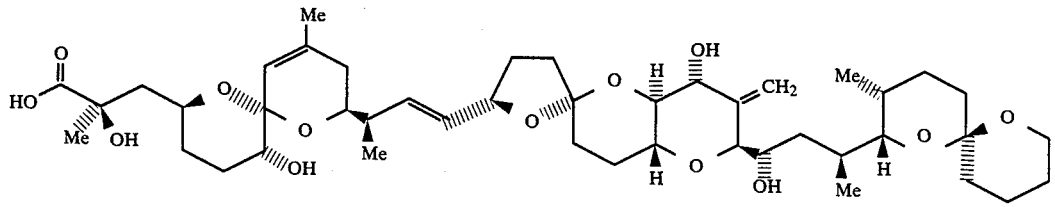

a salt thereof, or an ester thereof with glycine or a salt thereof.

According to still another aspect of the present invention, there is provided a pharmaceutical composition for treating and preventing cachexia and a side effect caused by TNF which comprises an effective amount of glycookadaic acid or its salt and a pharmaceutically acceptable carrier or diluent.

According to a still further aspect of the present invention, there is provided a method for treating and preventing cachexia and a side effect caused by TNF in a mammalian animal, including human, which comprises administering the animal glycookadaic acid or its salt.

DESCRIPTION OF THE PREFERRED EMBODIMENTS

Glycookadaic acid (1) Appearance and state

Colorless amorphous solid substance (2) Molecular weight 861 (measured by mass spectroscopy)

(3) Molecular formula

C$_{46}$H$_{71}$O$_4$N (4) Structural formula

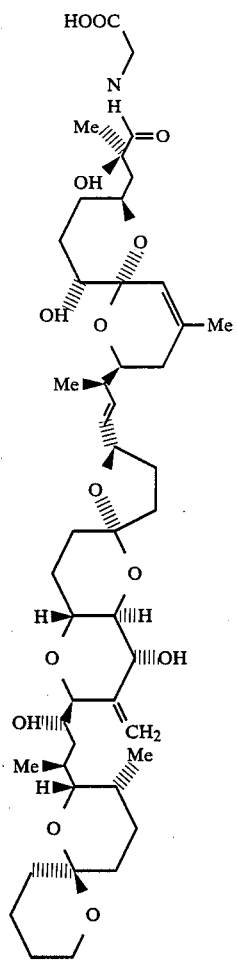

(5) Optical rotation $[\alpha]_D^{30}$ 25.3° (c=1.10, MeOH)

(6) Acid or base

Weekly acidic substance (7) Solubility

Easily soluble in methanol, ethanol or pyridine.

Insoluble or sparsely soluble in acetone or chloroform.

(8) Ultraviolet absorption spectrum

End absorption (measured in ethanol)

(9) Infrared absorption spectrum

Figure 1:
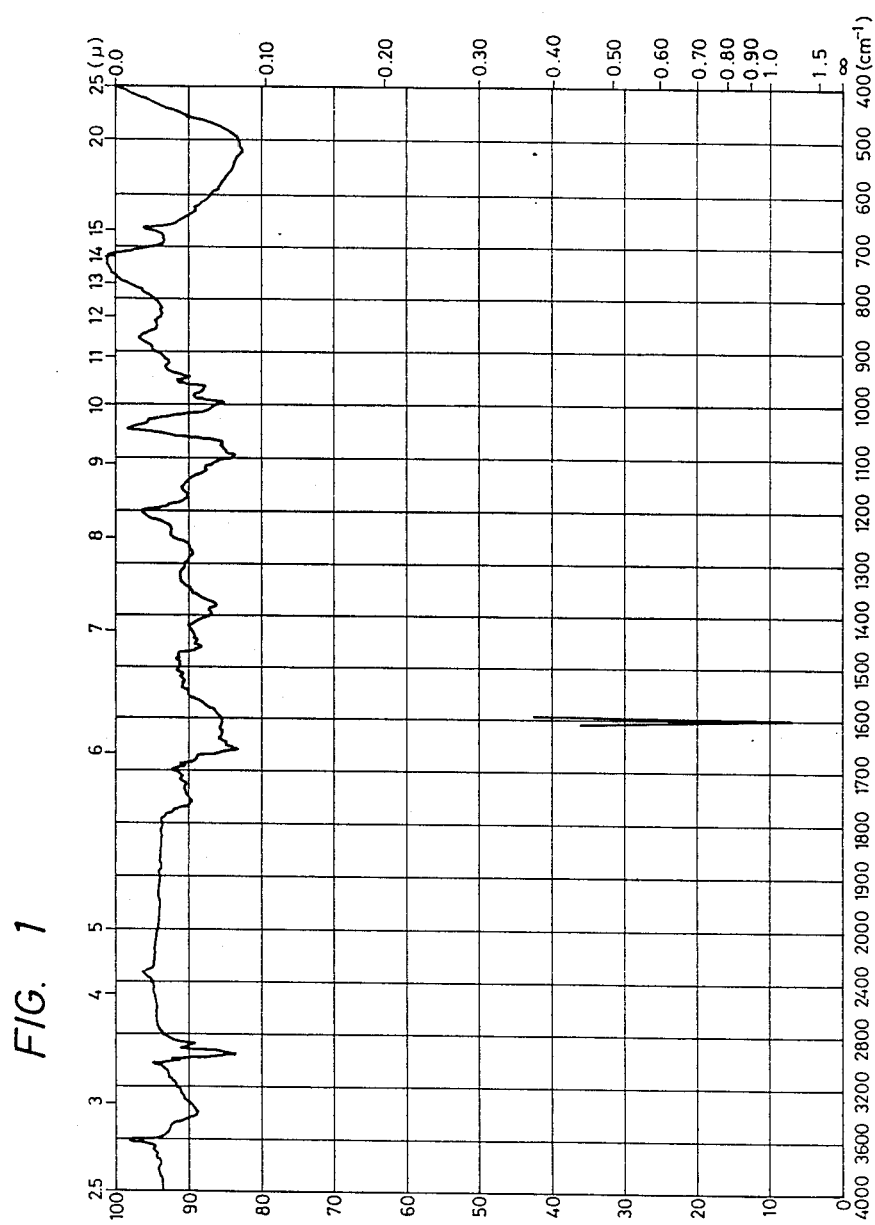
FIG. 1 shows an infrared spectrum of glycookadaic acid measured in chloroform.

See FIG. 1 (measured in CHCl$_3$)

(10) $^1$H-NMR spectrum (360 MHz)

Figure 2:
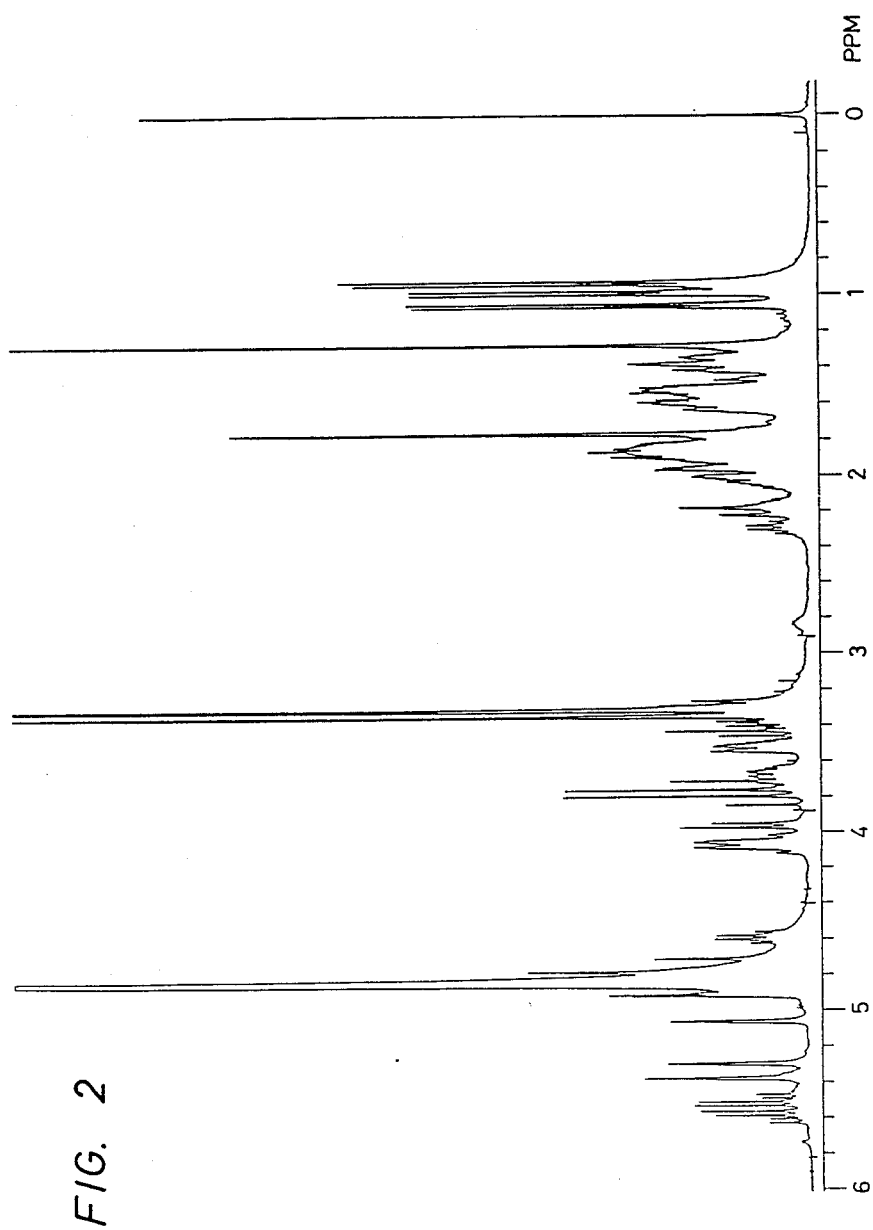
FIG. 2 shows $^1$H-NMR spectrum of glycookadaic acid measured in CD$_3$OD.

See FIG. 2 (measured in CD$_3$OD)

(11) $^{13}$C-NMR spectrum (25 MHz)

Figure 3:
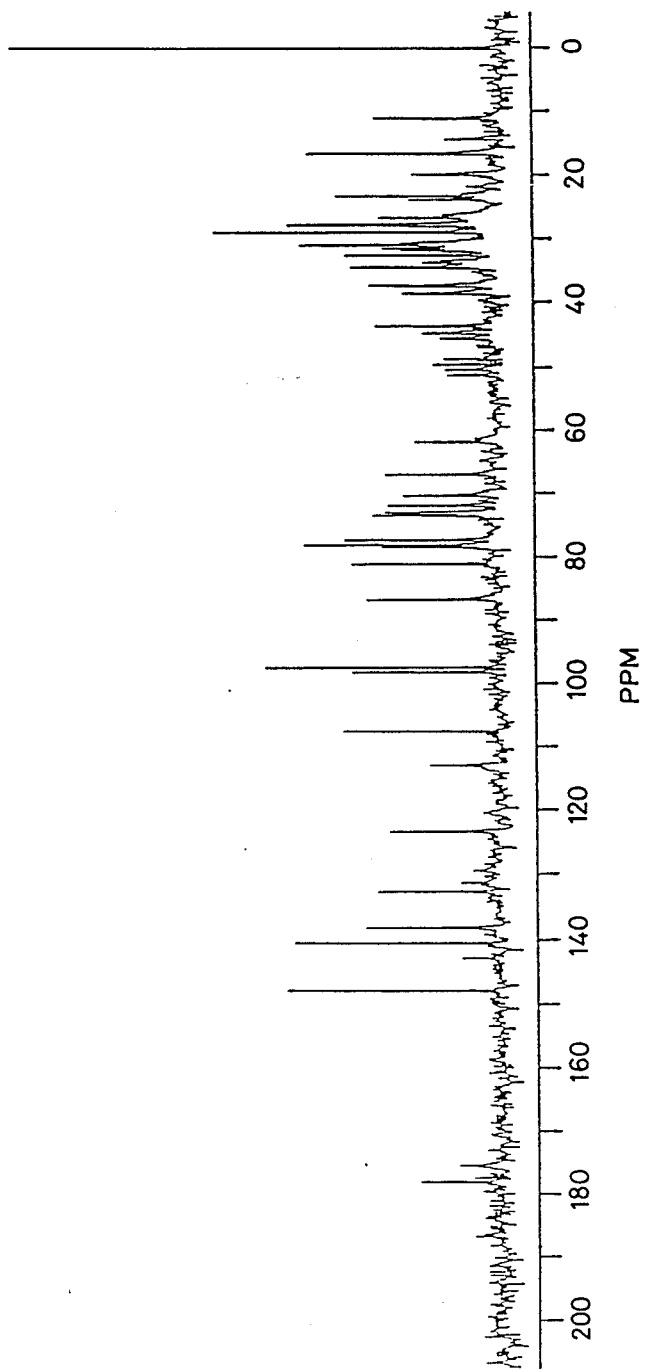
FIG. 3 shows $^{13}$C-NMR of glycookadaic acid measured in CDCl$_3$.

See FIG. 3 (measured in CDCl$_3$)

(12) Stability

Unstable to acid.

Relatively stable to alkali.

(13) Thin layer chromatography

Thin layer plate used:

| Developing solvent | Rf value |
|---|---|
| Methanol-chloroform (20:80) | 0.23 |
| Acetonitrile-water (50:50) | 0.36 |

HPTLC Plate No. 13728 with a concentration zone (manufactured by E. Merck)

The subject compound of the present invention, glycookadaic acid, can be produced by extraction and separation from *Halicondria okadai* Kadota and purification, as shown below.

Collected Halicondria okadai Kadota is rapidly frozen and then thawed, and small stones and the like are removed. Then the specimens of *Halicondria okadai* Kadota are ground in an organic solvent such as methanol, ethanol, propanol, butanol and the like by means of a blender, and the resulting solution is allowed to stand at a low temperature for 2-3 days. Then the solution is filtered to remove solid matters and the filtrate is concentrated under reduced pressure at a temperature lower than 45° C., extracted with butanol. A solvent mixture of 70% methanol-water and hexane is added to the resulting concentrate, stirred and then, the aqueous methanol layer is separated and concentrated at a temperature lower than 45° C. under reduced pressure. The oily matter thus obtained is purified by chromatography using an adsorbent such as TSK G300S resin (tradename, manufactured by Toyo Soda K.K.). As a developing solvent, there may be used a mixture of water and an alcohol such as methanol, ethanol and the like. The eluate is fractionized, and fractions exhibiting cytotoxicity are collected and concentrated under reduced pressure to give an oily material. The oily material is purified by using a reversed phase type column such as Lobar column (tradename, supplied by E. Merck). As a developing solvent, there is used a solvent mixture of acetonitrile and water. Eluted fractions containing glycookadaic acid are collected and concentrated under reduced pressure to give an oily matter containing glycookadaic acid. Then the oily matter is purified by silica gel column chromatography. As a developing solvent, there is used a mixture of ethanol and chloroform. Eluted fractions containing glycookadaic acid are collected and concentrated under reduced pressure to give an oily matter, which is then subjected to separation and purification by preparative thin layer chromatography (PTLC) using a mixture of ethanol and acetone as a developing solvent to produce a crude glycookadaic acid as a glass-like substance.

Finally, this amorphous substance is purified by a reversed phase type column using a mixture of acetonitrile and water as a developing agent such as Lobar column (tradename, manufactured by E. Merck) to give glycookadaic acid as a colorless amorphous solid substance.

On the other hand, glycookadaic acid of the present invention may be prepared chemically by using okadaic acid. For example, in a solvent not adversely affecting the reaction such as ethyl acetate, methylene chloride, acetone and the like, okadaic acid is reacted with a dehydrating agent such as 1,3-dicyclohexylcarbodiimide and the like and an active ester forming agent such as p-nitrophenol and the like at room temperature for 1-10 hours to form an active ester of okadaic acid, which is then reacted with glycine or its hydrochloride in the presence of one or more bases such as diethylamine, triethylamine, pyridine and the like to produce glycookadaic acid. The resulting glycookadaic acid can be easily isolated and purified by combining optionally conventional methods, for example, solvent extraction, concentration and chromatography.

Okadaic acid used as a starting material for preparing chemically glycookadaic acid is a compound having the following structure and can be easily isolated from *Halichondria okadai*

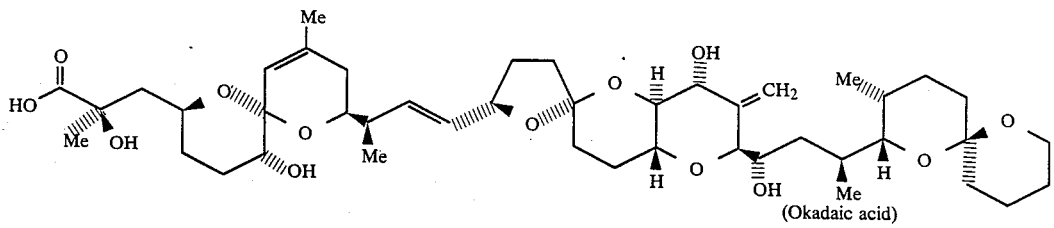
(Okadaic acid)

Kadota according to the method described in J. Am. Chem. Soc., 103, 2469-2471 (1981).

As salts of glycookadaic acid, there may be mentioned, for example, the salts of alkali metals such as sodium, lithium, potassium and the like, salts of alkaline earth metals such as calcium, magnesium and the like, and the salts with organic amines such as triethylamine, diethylamine and the like.

Pharmacological activity of glycookadaic acid of the present invention will be explained below. Hereinafter, glycookadaic acid and okadaic acid are referred to as "GOK" and "OK".

TEST EXAMPLE 1

Cytotoxicity

B-16 melanoma cell, P388 leukemia cell or L 929 cell was cultivated together with a prescribed amount of a test drug on a 24-well or 96-well test plate and the number of living cells was measured one day or 3 days later to know the 50% growth inhibition concentration.

The result is shown in Table 1 below. Cytotoxity of GOK is much weaker than that of OK.

TABLE 1

| | 50% growth inhibition concentration ($IC_{50}$) for various cells | | |
|---|---|---|---|
| | Cell species $IC_{50}$ (μg/ml) | | |
| Test drug | B-16 melanoma[1] | P388 leukemia | L 929 |
| GOK | 19 | —[2] | 28 |
| OK | 0.018 | 0.024 | 0.084 |

[1]Cultivated for one day
[2]Not tested

TEXT EXAMPLE 2

Acute toxicity

A test drug was injected into the peritoneal cavity of $BDF_1$ mouse (5 weeks old, female) to measure 50% lethal dose ($LD_{50}$).

The result is shown in Table 2. $LD_{50}$ of GOK is 100 times or more that of OK. Therefore, toxicity of GOK is so much weaker that GOK is a far safer drug than OK.

TABLE 2

| Test drug | 50% Lethal dose (LD$_{50}$) LD$_{50}$ (mg/kg) |
|---|---|
| GOK | >16 |
| OK | 0.16 |

TEXT EXAMPLE 3

Recovery effect of GOK on cachectin/TNF-induced reduction of lipoprotein lipase (LPL) in adipocytes 3T3-L1 cells ($5 \times 10^4$ cells per well) were cultivated in wells of 48-well test plate for about one week until the cell growth reached became confluent. Test drug and $4 \times 10^{-10}$ -10 g/ml (32 unit/ml as TNF activity) of recombinant human TNF (rHu-TNF) were added, and the cultivation was further continued.

After 20 hours, the test drug and rHu-TNF were removed. Then 10 unit/ml of heparin was added, and after 90 min., activity of lipoprotein lipase (LPL) isolated from 3T3-L1 cell by heparin was measured according to the method as described in Nelsson-Ehle, P., et al., J. Lipid Res., 17, 536 (1976).

On the LPL activity measured, the recovery on the reduction of lipoprotein lipase production was calculated by the following formula:

$$\frac{(rHu - TNF + \text{Test drug}) - (rHu - TNF)}{(\text{no treatment}) - (rHu - TNF)} \times 100(\%) \quad (A)$$

Note:
The value in the parentheses is an LPL activity in each case.

The result is shown in Table 3. GOK exhibited an effect of recovering from the lowering of production of lipoprotein lipase at 3-10 μg/ml, but OK did not exhibit the effect of inhibition even at a concentration of 0.1 μg/ml at which OK exhibits cytotoxicity.

TABLE 3

Recovery effect of GOK on cachectin/TNF-induced reduction of LPL in adipocytes

| Concentration of test drug (μg/ml) | Test drug GOK Experiment 1 | Test drug GOK Experiment 2 | OK |
|---|---|---|---|
| 0.001 | —$^a$ | —$^a$ | −2 |
| 0.01 | —$^a$ | —$^a$ | −3 |
| 0.1 | —$^a$ | 5 | −94 |
| 1.0 | 10 | 6 | −103 |
| 3.0 | 56 | 18 | —$^a$ |
| 10.0 | 38 | 79 | —$^a$ |
| 30.0 | —$^a$ | 20 | —$^a$ |

Note:
[1]The experiment was performed in the presence of rHu - TNF (32 unit/ml) exhibiting a 50% lowering of LPL production.
[2]"a" indicates the test was not carried out.

TEST EXAMPLE 4

Effect on cytotoxic activity of TNF

L 929 cells ($10^4$ cells/well) was cultivated on a test plate having 96 wells, and after 24 hours, a test drug and recombinant human-tumor necrosis factor (rHu - TNF) were added thereto such that rHu - TNF became $2.5 \times 10^{-11}$ g/ml (TNF activity of 2 unit/ml), and then, after 24 hours, the number of living cells was measured.

The effect of test drug on the cytotoxicity of TNF was calculated according to the above-mentioned formula (A) and shown by "%" value.

The results are shown in Table 4. Neither GOK nor OK affected the cytolytic activity of TNF.

TABLE 4

| Concentration of test drug (μg/ml) | Test drug GOK | Test drug OK |
|---|---|---|
| 0.001 | —$^a$ | −5 |
| 0.01 | 3 | −6 |
| 0.1 | 1 | −9 |
| 1.0 | 3 | −33 |
| 10.0 | 15 | —$^a$ |

Note:
[1]The experiments were effected in the presence of TNF (2 units/ml) exhibiting 75% cytotoxicity.
[2]"a" indicates that the test was not made.

In view of the foregoing, it has been found that the toxicity of GOK is low, and does not suppress the cytotoxic activity of cachectin/TNF toward cancer cells, but specifically recovers the lowering effect on the generation of lipoprotein lipase in adipocytes.

In case of patients with cancer or infective diseases, there are observed general infirmities such as weight reduction, inappetence, dysbolism, and the like, in addition to fever, chills, trepidation, and hypotension.

These syndromes are called cachexia. It is considered that a part of the cause of the cachexia is abnormal lipid metabolism represented by lowered production of lipoprotein lipase (LPL) caused by cachectin which macrophages produce due to stimulus of endotoxin.

Glycookadaic acid of the present invention specifically recovers lowering of production of lipoprotein lipase (LPL) by cachectin/TNF, and therefore, glycookadaic acid can be used for preventing or treating cachexia observed in cancer or other diseases and adverse reactions due to TNF.

In addition, it is known that recombinant interleukin 1 and recombinant interferons cause lowering of production of lipoprotein lipase (Patton, J.S., et al., Proc. Natl. Acad. Sci. USA, 83, 8313-8317 (1986); Beutler, B.A., et al., J. Immunol., 135, 3969-3971 (1985)).

It is also known that interferons exhibit adverse reactions such as fever, chills, lassitude, inappetence, general weekening and hypotension (Furue, H., Jpn. J. Cancer Chemoth., 11, 186-187 (1984); Rohatiner, A.Z.S., et al., Cancer Chemother. Pharmacol., 9, 97-102 (1982)). Glycookadaic acid of the present invention is effective against adverse reactions caused by interleukin 1 and interferons.

TNF produced by macrophage is called TNF-β while TNF produced by lymphocytes is called TNF-β(Shalaby, M.R., et al., J. Immunol., 135, 2069-2073 (1985)).

Since the TNF-α and the TNF-β have many common amino acid sequences, as well as almost the same cytotoxic effect on cancer cells, it is predictable that TNF-β also exhibits adverse reactions similar to those of TNF-α. Glycookadaic acid of the present invention appears to be effective as an agent for treating such adverse reactions.

Glycookadaic acid of the present invention may be given by oral or rectal administration or injection. When an injectable preparation is produced, pH controlling agents, buffer agents, stabilizing agents, and/or excipients may be added to glycookadaic acid, the main drug. Further, according to conventional technique, lyophilized injectable preparations may be produced, and there can be produced preparations for subcutaneous, intramuscular or intravenous injection.

Orally admisterable solid preparations may be produced by adding excipients, if desired, further binding agents, disintegrators, lubricating agents, coloring agents, and/or flavoring agents, and the like to the main drug, and forming tablets, coated tablets, granules, powders or capsules according to conventional technique.

Oral liquid pharmaceuticals may be prepared by adding flavoring agents, buffer agents, and/or stabilizers to the main drug and forming syrup or dry syrup.

Rectal suppository may be prepared by adding excipients, if desired, further surfactants to the main drug to form rectal suppository according to conventional technique.

It is also possible to incorporate TNF as an active agent other than the main drug to the abovementioned administrating formulas.

The dosage levels differ depending on conditions, age, body weight, and administration forms. Dosage levels of the order of about 50-500 mg per body per day are useful for injection though the dosage levels differ from portion to portion to be administered. When administered orally or rectally in the form of suppository, the dosage levels are about 100-1,000 mg per body per day. The dosage levels may be changed according to description of doctor.

The following examples are given for illustrating the present invention.

EXAMPLE 1

600 kg of Halichondria okadai Kadota collected at Aburatsubo, Miura peninsula, Kanagawa-ken, Japan was ground in 500 l. of methanol with a blender and soaked in the methanol at low temperature for 2-3 days, and then the solid matter was removed by filtration.

The resulting filtrate was concentrated by a flash evaporator (or vacuum) at a temperature lower than 45° C. to produce about 10 l. of a water-containing extract. The extract was extracted three times with 2 l. of water-saturated n-butanol. The resulting liquid extracts were combined and concentrated under reduced pressure. To the resulting liquid concentration were added 3 l. of 70% methanol-water and 1 l. of n-hexane, shaked, and the aqueous methanol layer was taken out, washed further twice with each 1 l. of n-hexane and concentrated under reduced pressure. The oily matter thus obtained was suspended in a small amount of a 20% aqueous ethanol, and then added to a column (3.5 ID×3 cm) packed with 250 ml of TSK G3000 S (tradename, manufactured by Toyo Soda K.K.) washed with ethanol and then water.

After the column was washed with 2 l. of a 40% aqueous ethanol, the elution was effected with 2 l. of a 50% aqueous ethanol and then 4 l. of a 60% aqueous ethanol to collect the fractions containing glycookadaic acid and concentrated under reduced pressure. The resulting oily matter was added to a Lobar column (tradename) (LiChroprep RP 8 column size C) (tradename, manufactured by E. Merck), developed with a 40% acetonitrile-water, and fractions, No. 39-No. 63 (20 ml each), containing glycookadaic acid were collected and concentrated under reduced pressure to obtain 355 mg of an oily matter. The oily matter was added to a column (2.5 ID×15 cm) packed with silica gel (No. 7734 Silica gel 60, manufactured by E. Merck), and subsequently developed with 100 ml of chloroform, 100 ml of 5% ethanol-chloroform, 200 ml of 15% ethanol-chloroform and 100 ml of 20% ethanol-chloroform to collect fractions containing glycookadaic acid followed by concentrating under reduced pressure to produce 89 mg of an oily material.

The oily material was purified by preparative thin layer chromatography (PTLC) (No. 13895 Silica Gel 60F 254, manufactured by E. Merck) using ethanol-acetone (18:82) as a developing solvent to produce crude glycookadaic acid (36.9 mg) in a glass-like form. The resulting glass-like material was applied to a Lobar column (tradename) (Lichroprep RP-8 Column size A) equilibrated preliminarily by using 15% acetonitrilewater, developed with 15% acetonitrile-water as a developing solvent at a flow-rate of 2.0 ml/min to collect eluates containing glycookadaic acid followed by concentrating under reduced pressure to give 28.4 mg of pure glycookadaic acid as a amorphous solid material.

The detection of glycookadaic acid at each purification step was effected by means of HPTLC using methanol-chloroform (20:80) as a developing solvent and an anisaldehyde sulfuric acid type color developing agent as a color developing agent (Glycookadaic acid give a red or brown spot at Rf 0.23 in this HPTLC.).

EXAMPLE 2

90 mg of okadaic acid and 334 mg of p-nitrophenol were dissolved in 10 ml of ethyl acetate, and 148 mg of 1,3-dicyclohexylcarbodiimide (DCC) was added to the resulting solution followed by stirring at room temperature for 12 hours. The resulting reaction mixture was washed with 10 ml each of water three times, and the ethyl acetate layer was concentrated under reduced pressure and subjected to a preparative thin layer chromatography using 10% methanol-chloroform as a developing solvent to give p-nitrophenyl ester of okadaic acid (49.5 mg).

The ester was dissolved in 5 ml of pyridine, and 40 mg of glycine was added thereto followed by stirring over night. The resulting reaction mixture was concentrated and then subjected to a preparative thin layer chromatography (PTLC) (No. 13895 Silica Gel 60F254, manufactured by E. Merck) using methanol-chloroform (20:80) as a developing solvent to separate and purify the product resulting in glycookadaic acid in the colorless glass solid form, 42.8 mg (yield 44.4%).

What we claim is:

1. A compound having the formula,

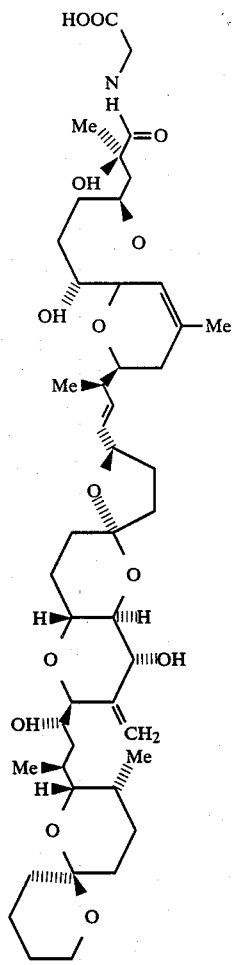 [I]

or a pharmaceutically acceptable salt thereof substantially free from other components of *Halicondria okadai*.

2. Pharmaceutical composition for treating cachexia-like side effects caused by TNF which comprises an effective amount of the compound of claim 1 and a pharmaceutically acceptable carrier or diluent.

3. Method of treating cachexia-like side effects caused by TNF in a mammalian animal, including humans, which comprises administering to the animal an effective amount of the compound of claim 1.

* * * * *

UNITED STATES PATENT AND TRADEMARK OFFICE
CERTIFICATE OF CORRECTION

PATENT NO. : 4,835,176

DATED : May 30, 1989

INVENTOR(S) : Daisuke UEMURA et al.

It is certified that error appears in the above-identified patent and that said Letters Patent is hereby corrected as shown below:

Column 1, line 55, change "IF" to --INF--.

Column 4, line 42, change "$[\alpha]_o 30\ 25.3°\ (c=1.10,\ MeOH)$" to --$[\alpha]_o + 25.3°\ (c-1.10,\ MeOH)$--.

Column 7, lines 10-12, should read as one continuous line.

Column 7, line 16, change "$4 \times 10^{-10} - 10\ g/ml$" to --$4 \times 10^{-10}\ g/ml$--.

Column 8, in Notes of Table 4, change "(2 units/ml)" to --(2 unit/ml)--.

Column 8, line 49, change "TNF-β while TNF" to --TNF-α while TNF--.

Column 8, line 53, change "TNF-α and" to --TNF-α and--.

In Claim 1, amend the chemical formula as follows:

UNITED STATES PATENT AND TRADEMARK OFFICE
CERTIFICATE OF CORRECTION

PATENT NO. : 4,835,176

DATED : May 30, 1989

INVENTOR(S) : Daisuke UEMURA et al.

It is certified that error appears in the above-identified patent and that said Letters Patent is hereby corrected as shown below:

In Claim 1, amend the chemical formula as follows:

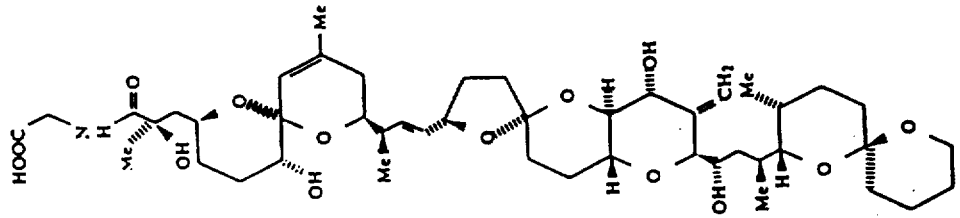

Signed and Sealed this

Twenty-ninth Day of May, 1990

*Attest:*

HARRY F. MANBECK, JR.

*Attesting Officer*      *Commissioner of Patents and Trademarks*